US00PP35036P2

(12) United States Plant Patent
Mathey

(10) Patent No.: US PP35,036 P2
(45) Date of Patent: Mar. 14, 2023

(54) ***GARDENIA* PLANT NAMED 'SMNGDUO'**

(50) Latin Name: *Gardenia jasminoides*
Varietal Denomination: SMNGDUO

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/953,012

(22) Filed: Sep. 26, 2022

(51) Int. Cl.
*A01H 5/02* (2018.01)
*A01H 6/76* (2018.01)

(52) U.S. Cl.
USPC ..... Plt./255
CPC ..... *A01H 6/76* (2018.05)

(58) Field of Classification Search
USPC ..... Plt./255
CPC ..... A01H 6/76; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Gardenia* plant named 'SMNGDUO', characterized by its low mounding, upright to outwardly spreading plant habit; moderately vigorous growth habit and moderate growth rate; glossy dark green-colored leaves; freely and continuously flowering from mid to late summer; relatively large double-type white-colored flowers; and good garden performance.

2 Drawing Sheets

Figure 1:
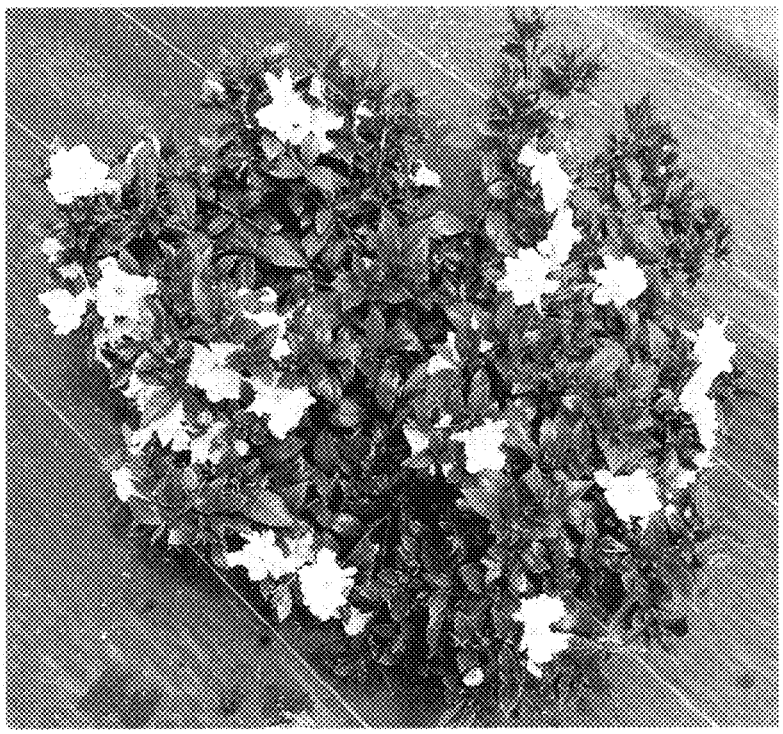

Botanical designation: *Gardenia jasminoides.*
Cultivar denomination: 'SMNGDUO'.

BACKGROUND OF THE INVENTION

The present Invention relates to a new and distinct cultivar of *Gardenia* plant, botanically known as *Gardenia jasminoides*, commonly referred to as Common *Gardenia* or Cape Jasmine, and hereinafter referred to by the name 'SMNGDUO'.

The new *Gardenia* plant is a product of a planned breeding program conducted by the Inventor in Grand Haven, Mich. The objective of the breeding program was to develop new low mounding *Gardenia* varieties with large and attractive flowers.

The new *Gardenia* plant originated from an open-pollination in 2013 of an unidentified proprietary *Gardenia jasminoides* selection, not patented, as the female, or seed, parent with an unknown proprietary *Gardenia jasminoides* selection as the male, or pollen, parent. The new *Gardenia* plant was discovered and selected by the Inventor as a single flowering plant within the progeny of the stated open-pollination in a controlled outdoor nursery environment in Grand Haven, Mich. in 2017.

Asexual reproduction of the new *Gardenia* plant by softwood cuttings in Grand Haven, Mich. since 2017 has shown that the unique features of this new *Gardenia* plant are stable and reproduced true to type in successive generations of asexual reproduction.

SUMMARY OF THE INVENTION

Plants of the new *Gardenia* have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'SMNGDUO'. These characteristics in combination distinguish 'SMNGDUO' as a new and distinct *Gardenia* plant:

1. Low mounding, upright to outwardly spreading plant habit.
2. Moderately vigorous growth habit and moderate growth rate.
3. Glossy dark green-colored leaves.
4. Freely and continuously flowering from mid to late summer.
5. Relatively large double-type white-colored flowers.
6. Good garden performance.

Plants of the new *Gardenia* differ from plants of the female parent selection in the following characteristics:

1. Plants of the new *Gardenia* are more low mounding than and not as upright as plants of the female parent selection.
2. Flowers of plants of the new *Gardenia* are larger than flowers of plants of the female parent selection.

Plants of the new *Gardenia* can also be compared to plants of *Gardenia jasminoides* 'Prince Charles', disclosed in U.S. Plant Pat. No. 29,304. In side-by-side comparisons, plants of the new *Gardenia* differ from plants of 'Prince Charles' in the following characteristics:

1. Plants of the new *Gardenia* are more vigorous than plants of 'Prince Charles'.
2. Flowers of plants of the new *Gardenia* are larger than flowers of plants of 'Prince Charles'.

BRIEF DESCRIPTION OF THE PHOTOGRAPHS

The accompanying colored photographic sheet illustrates the overall appearance of the new *Gardenia* plant showing the colors as true as it is reasonably possible to obtain in colored reproductions of this type. Colors in the photograph may differ slightly from the color values cited in the detailed botanical description which accurately describe the colors of the new *Gardenia* plant.

The photograph on the first sheet (FIG. 1) is a top perspective view of a typical plant of 'SMNGDUO' grown in a container.

Figure 2:
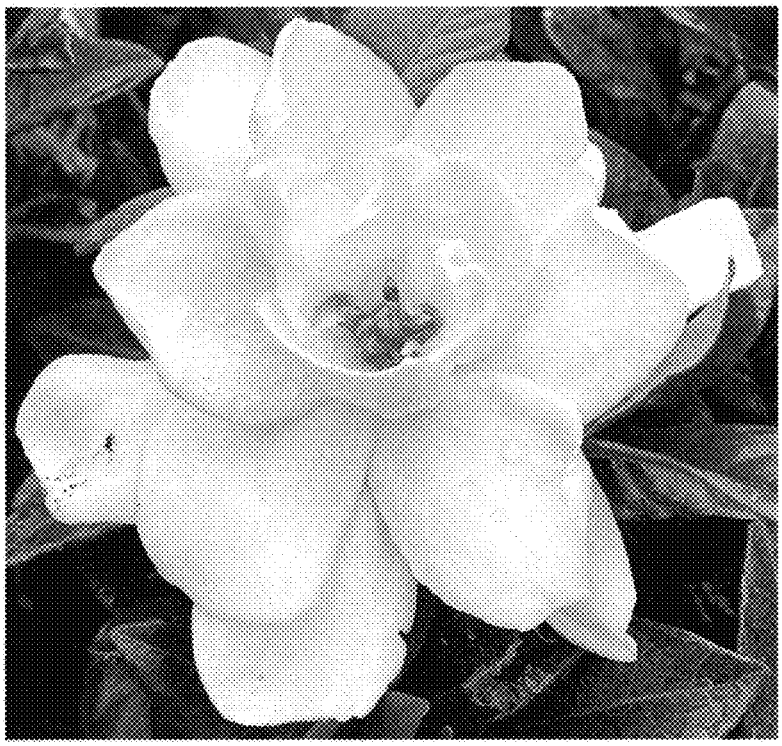

The photograph on the second sheet (FIG. 2) is a close-up view of a typical flower of 'SMNGDUO'.

DETAILED BOTANICAL DESCRIPTION

The aforementioned photographs, following observations and measurements describe plants grown during the early summer in three-gallon containers in a polyethylene-covered greenhouse in Grand Haven, Mich. and under typical *Gardenia* production practices. Plants were three years old when the photographs and the description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Gardenia jasminoides* 'SMNGDUO'.

Parentage:

*Female, or seed, parent.*—Unidentified proprietary selection of *Gardenia jasminoides*, not patented.

*Male, or pollen, parent.*—Unknown proprietary selection of *Gardenia jasminoides*, not patented.

Propagation:

*Type.*—By softwood cuttings.

*Time to initiate roots, summer.*—About 30 to 45 days at temperatures about 18° C. to 27° C.

*Time to produce a rooted young plant, summer.*—About six weeks at temperatures about 18° C. to 27° C.

*Root description.*—Medium in thickness, fleshy and fibrous; orangish white to tan in color, actual color of the roots is dependent on substrate composition, water quality, fertilizers, substrate temperature and age of roots.

*Rooting habit.*—Freely branching; medium density.

Plant description:

*Plant and growth habit.*—Perennial shrub; low mounding upright to outwardly spreading plant form; moderately vigorous growth habit and moderate growth rate.

*Plant height.*—About 25 cm.

*Plant width* (*spread*).—About 65 cm.

*Lateral branches.*—Quantity per plant: About 20 per plant; pruning will enhance lateral branch development. Length: About 25 cm. Diameter: About 5 mm. Internode length: About 3 cm. Texture, developing: Slightly pubescent. Texture, developed: Smooth, glabrous. Aspect: About 20° to 45° from vertical. Strength: Strong. Color, developing: Close to 144A. Color, developed: Close to 197B.

Leaf description:

*Arrangement.*—Opposite; single.

*Length.*—About 7 cm.

*Width.*—About 3.5 cm.

*Shape.*—Elliptic.

*Apex.*—Acuminate.

*Base.*—Attenuate.

*Margin.*—Entire.

*Texture and luster, upper surface.*—Smooth, glabrous; glossy coriaceous.

*Texture and luster, lower surface.*—Smooth, glabrous with prominent venation; somewhat glossy.

*Venation pattern.*—Pinnate.

*Color.*—Developing leaves, upper and lower surfaces: Close to 144A. Fully expanded leaves, upper surface: Close to NN137A; venation, close to 144B. Fully expanded leaves, lower surface: Close to 147B; venation, close to 144B.

*Petioles.*—Length: About 5 mm. Diameter: About 2 mm. Strength: Moderately strong. Texture, upper and lower surfaces: When developing, slightly pubescent becoming smooth and glabrous with development. Color, upper surface: Close to NN137A. Color, lower surface: Close to 147B.

Flower description:

*Flower type, arrangement and quantity.*—Relatively large, symmetrical rotate double-type flowers; flowers axillary and solitary; about four to ten flowers and flower buds per lateral stem and about 300 flowers develop per plant; flowers face upright to outwardly; flowers persistent.

*Flowering season.*—Plants of the new *Gardenia* flower from mid to late summer in an outdoor nursery in Grand Haven, Mich.

*Flower diameter.*—About 6.5 cm.

*Flower depth* (*height*).—About 2 cm.

*Fragrance.*—Moderately to strongly fragrant; fragrance is sweet, bright and peppery.

*Flower buds.*—Length: About 2 cm. Diameter: About 1 cm. Shape: Oblong. Texture: Smooth, glabrous. Color: Close to 144A.

*Petals.*—Quantity and arrangement: About six per flower arranged in two whorls; petals are fused at the base. Length: About 3 cm. Width: About 2 cm. Shape: Obovate. Apex: Obtuse. Margin: Entire. Texture, upper and lower surfaces: Smooth, glabrous; soft, silky. Color: When opening, upper and lower surfaces: Close to NN155B. Fully opened, upper and lower surfaces: Close to NN155B; venation, close to NN155B; color does not change with subsequent development.

*Petaloids.*—Quantity and arrangement: About ten to twelve in two whorls. Outer whorl petaloids: Length: About 2.5 cm. Width: About 2 cm. Shape: Elliptic. Apex: Obtuse. Base: Obtuse. Margin: Mostly entire with occasional notches; somewhat undulate. Texture, upper and lower surfaces: Smooth, glabrous; soft and silky. Color: When opening, upper and lower surfaces: Close to NN155B. Fully opened, upper and lower surfaces: Close to NN155B; venation, close to NN155B; color does not change with subsequent development. Inner whorl petaloids: Length: About 2 cm. Width: Variable, about 1 cm to 2 cm. Shape: Elliptic to somewhat variable in shape. Apex: Variable, obtuse or notched, undulate. Base: Obtuse. Margin: Irregular notches; undulate. Texture, upper and lower surfaces: Smooth, glabrous; soft and silky. Color: When opening, upper and lower surfaces: Close to NN155B. Fully opened, upper and lower surfaces: Close to NN155B; venation, close to NN155B; color does not change with subsequent development.

*Sepals.*—Quantity per flower: Typically six in a single whorl; fused at the base. Length: About 2 cm. Width: About 3 mm. Shape: Roughly linear. Apex: Acute. Margin: Entire. Texture, upper and lower surfaces: Smooth, glabrous. Color, upper and lower surfaces: Close to 144A.

*Peduncles.*—Length: About 1 cm. Diameter: About 3 mm. Strength: Strong. Aspect: About 45° from stem axis. Texture: Smooth, glabrous. Color: Close to 144A.

*Reproductive organs.*—Stamens: To date, no true stamens have been observed on plants of the new *Gardenia*; occasionally, partially transformed inner whorl petaloids are observed with stamen-like characteristics. Pistils: Pistil quantity per flower: One. Pistil length: About 7 mm. Stigma shape: Irregularly two to three-lobed. Stigma color: Close to 160C.

*Fruits and seeds.*—To date, fruit and seed development have not been observed on plants of the new *Gardenia.*

Pathogen & pest tolerance: To date, plants of the new *Gardenia* have not been observed to be tolerant to pathogens and pests common to *Gardenia* plants.

Garden performance: Plants of the new *Gardenia* have been observed to have good garden performance and to tolerate temperatures ranging from −31° C. to 38° C.

It is claimed:

1. A new and distinct *Gardenia* plant named 'SMNGDUO' as illustrated and described.

* * * * *